(12) United States Patent
Fraisse et al.

(10) Patent No.: US 8,304,440 B2
(45) Date of Patent: Nov. 6, 2012

(54) COMBINATION OF A BIS-THIAZOLIUM SALT OR A PRECURSOR THEREOF AND ARTEMISININ OR A DERIVATIVE THEREOF FOR TREATING ACUTE MALARIA

(75) Inventors: Laurent Fraisse, Paris (FR); Henri Vial, Paris (FR); Sharon Aurore Wein, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/851,747

(22) Filed: Aug. 6, 2010

(65) Prior Publication Data

US 2011/0160254 A1    Jun. 30, 2011

Related U.S. Application Data

(63) Continuation of application No. PCT/FR2009/000129, filed on Feb. 5, 2009.

(30) Foreign Application Priority Data

Feb. 6, 2008  (FR) ...................................... 08 00618

(51) Int. Cl.
  *A61K 31/425* (2006.01)
  *A61K 31/335* (2006.01)
  *A61K 31/35* (2006.01)
(52) U.S. Cl. .................. 514/365; 514/452; 514/453
(58) Field of Classification Search .................. 514/365, 514/452, 453
  See application file for complete search history.

(56) References Cited

U.S. PATENT DOCUMENTS 5,677,331 A * 10/1997 Zhou et al. ..................... 514/450
6,972,343 B1 * 12/2005 Vial et al. ....................... 564/154

FOREIGN PATENT DOCUMENTS

| FR | 2796642 | 1/2001 |
| FR | 2884715 | 10/2006 |
| WO | WO 01/05742 | 1/2001 |
| WO | WO 2006/111647 | 10/2006 |

OTHER PUBLICATIONS

West, Solid state chemistry and its application, Wilsy, New York, 1988. pp. 358, 365.*
Vippagunta et al. "Crystalline solid," Advanced, drug, Delivery, 2001, vol. 48, pp. 3-26.*
Ulrich "Crystallization," Chapter 4, Kirk-Othmer Encyclopedia of Chemical techology, John, Wiley and Sons, 2002.*
Mutabingwa "Artemisinin-based combination therapies (ACTs): Best hope for malaria treatment but inaccessible to the needy," Acta Tropica 95 (2005) pp. 305-315.*
Taudon, N., et. al., Quantitive Analysis of a Bis-Thiazolium Antimalarial Compound, SAR97276, in Mouse Plasma and Red Blood Cell Samples. Using Liquid Chromatography Mass Spestrometry, Journal of Pharmaceutical and Biomedical Analysis, vol. 46, (2008), pp. 148-156.

(Continued)

*Primary Examiner* — Shengjun Wang
(74) *Attorney, Agent, or Firm* — Ronald G. Ort

(57) ABSTRACT

The present invention relates to a combination of antimalarial active ingredients, namely a bisthiazolium salt or a precursor thereof and artemisinin or derivatives thereof. The invention also relates to a pharmaceutical composition comprising such a combination and use thereof in the treatment and/or prevention of malaria.

15 Claims, 3 Drawing Sheets

OTHER PUBLICATIONS

Ancelin, M. L. et. al., In Vivo Antimalarial Activities of Mon- and Bis Quatemary Ammonium Salts Interfering with Plasmodium Phospholipid Metabolism, Antimicrobial Agents and Chemotherapy, vol. 47, No. 8, pp. 2598-2605, (2003).

Barkan, D., et. al., Optimisation of Flow Cytometric Measurement of Parasitaemia in Plasmodium-Infected Mice, International Journal for Parasitology, vol. 30, (2000), pp. 649-653.

Colin J. Sutherland et al., The addition of artesunate to chloroquine for treatment of plasmodium falciparum malaria in gambian children delays, but does not prevent treatment failure, Am. J. Trop. Med. Hyg. (2003, pp. 19-25, vol. 69, No. 1.

Gelb, M. H., et. al., Drug Discovery for Malaria: A Very Challenging and Timely Endeavor, Current Opinion in Chemical Biology. (2007), vol. 11, pp. 440-445.

Hamze, A., et. al., Mono- and Bis-Thiazolium Salts Have Potent Antimalarial Activity, J. Med. Chem., (2005), vol. 48, pp. 3639-3643.

J.H. Portus et al., The Chemoterapy of Rodent Malaria, XXII, Annals of Tropical Medicine and Parasitology (1975, pp. 155-171, vol. 69, No. 2.

Kofoed et al, No Benefits from Combining Chloroquine With Artesunate for Three Days for Treatment of Plasmodium Falciparum in Guinea-Bissau, Transactions of the Royal Society of Tropical Medicine and Hygiene (2003) 97, 429-433.

Richier, E., et. al., Potent Antihematozoan Activity of Novel Bisthiazolium Drug T16: Evidence for Inhibition of Phosphatidylcholine Metabolism in Erythrocytes Infected with Babesia and Plasmodium spp., Antimicrobial Agents and Chemotherapy, vol. 50. No. 10, pp. 3381-3888, (2006).

International Search Report for WO2009/115666A3 mailed on Nov. 5, 2009.

Snyder, C., et. al., In Vitro and In Vivo Interaction of Synthetic Peroxide RBx11160 (OZ277) With Piperaquine in Plasmodium Models, Experimental Parasitology, vol. 115, (2007), pp. 296-300.

\* cited by examiner

Figure 1 - Change in parasitemia during and after 4 days of ip treatment with artesunate (AS)
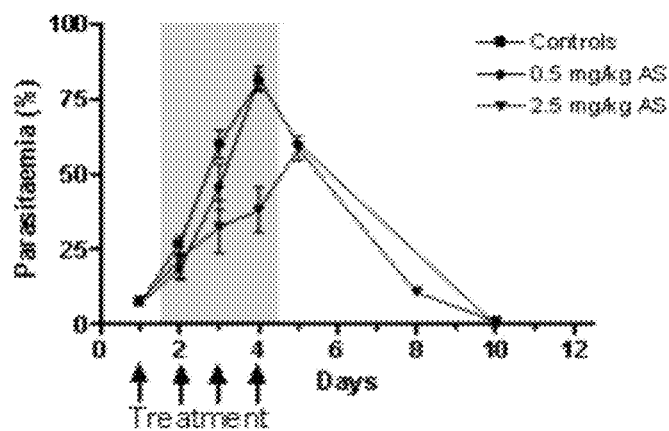
Figure 2 - Change in parasitemia during and after 4 days of ip treatment with T3
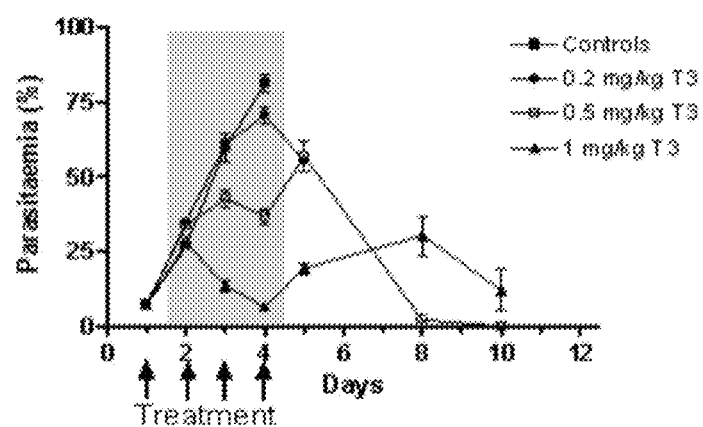

Figure 3 - Change in parasitemia during and after 4 days of ip treatment with 0.2 mg/kg/d of T3 and 2.5 mg/kg/d of artesunate (AS)
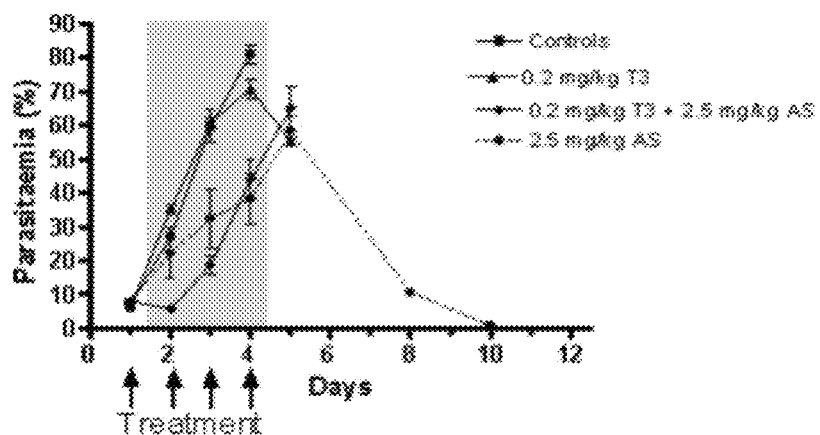
Figure 4 - Change in parasitemia during and after 4 days of ip treatment with 0.5 mg/kg/d of T3 and 2.5 mg/kg/d of artesunate (AS)
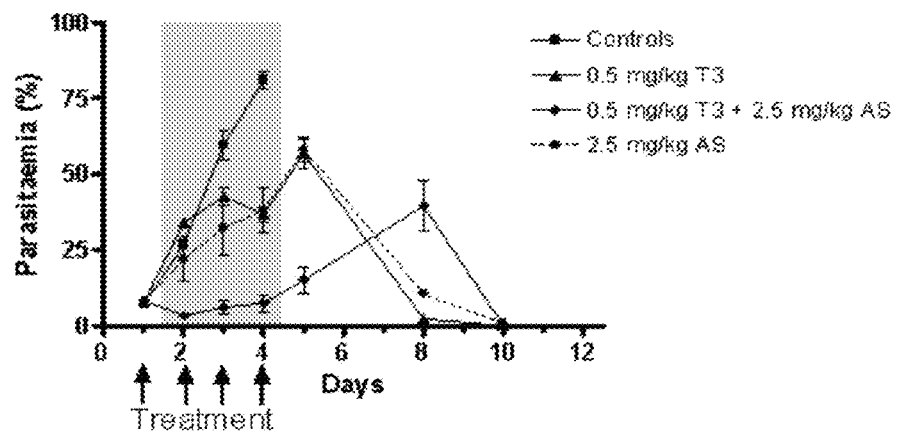

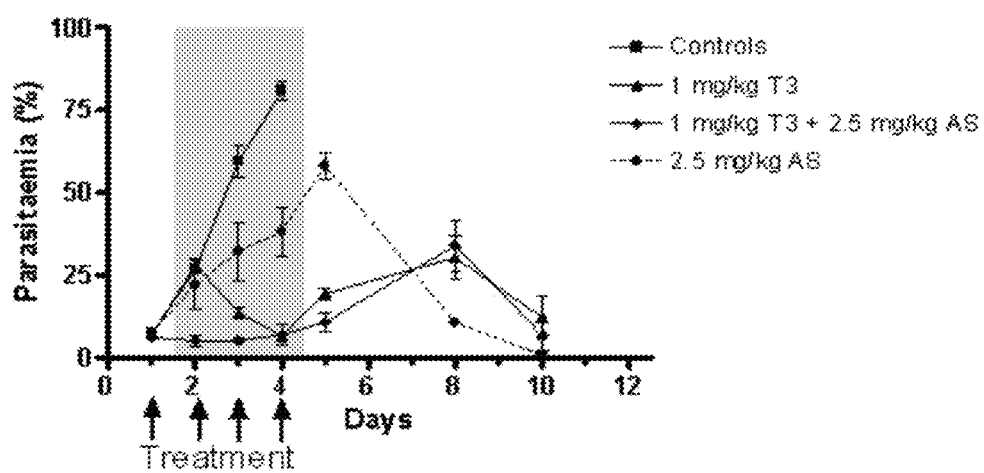
Figure 5 - Change in parasitemia during and after 4 days of ip treatment with 1 mg/kg/d of T3 and 2.5 mg/kg/d of artesunate (AS)

COMBINATION OF A BIS-THIAZOLIUM SALT OR A PRECURSOR THEREOF AND ARTEMISININ OR A DERIVATIVE THEREOF FOR TREATING ACUTE MALARIA

The present invention relates to a novel combination of antimalarial active ingredients, namely a bisthiazolium salt or a precursor thereof and artemisinin or derivatives thereof, and also to a pharmaceutical composition comprising such a combination, of use in the treatment and/or prevention of malaria.

Malaria is one of the primary infectious causes of mortality in the world and annually affects more than 500 million individuals, among whom 1.5 to 3 million die each year. This scourge affects mainly sub-Saharan Africa, south-east Asia and Latin America.

Four types of parasites of the *Plasmodium* genus (*P. falciparum, P. malariae, P. vivax* and *P. ovale*), transported by *Anopheles* mosquitoes, propagate malaria. *Plasmodium falciparum*, which is widespread in Africa, is the most virulent parasite and is responsible for most of the lethal forms of the disease.

The strong upsurge in the disease observed over the last few years is due to several factors, among which is the resistance of many strains of *Plasmodium falciparum* to the medicaments currently used, such as chloroquine, mefloquine, amodiaquine or else the antifolics and antifolinics, such as pyrimethamine and sulfadoxine.

Many individuals suffering from malaria exhibit an acute infection, with few revealing physical signs apart from a slight anemia and an increase in volume of the spleen (splenomegaly). The symptoms depend on the variety of malaria. Nevertheless, the general clinical characteristics are: feeling unwell, hyperthermia (fever), headaches, digestive problems such as nausea, vomiting and/or abdominal pain, diarrhea, asthenia, muscle pain, arthralgia (joint pain) and jaundice, in particular.

The treatment is generally carried out by administration of chloroquine (or of basic quinine hydrochloride in the event of resistance to chloroquine) until an improvement and disappearance of the parasites in the blood are obtained (usually between 3 and 5 days). The patient then generally takes a single medicament constituted of 1.5 grams of sulfadoxine and 75 mg of pyrimethamine.

Other treatments based on antifolics and on antifolinics, or alternatively based on malarone, are also used.

Severe malaria caused by *Plasmodium falciparum* is a cerebral malaria which combines a substantially elevated temperature (40° C.) and a coma which has a poor prognosis despite the treatment and for which mortality sometimes rises to 20% in adults and 15% in children. The appearance of severe malaria is either gradual or abrupt. It begins after instantaneous and transient convulsions of one or more muscles, followed by decontractions. They are localized or generalized throughout the body. This variety of malaria is accompanied by nystagmus (incessant jumping of the eyes from side to side), sometimes by a stiff neck and by a disturbance of the reflexes. Severe malaria can also be accompanied by retinal bleeding, hypoglycemia, pulmonary edema, kidney involvement, anemia and/or hematemesis (reflux of blood originating from the damaged organs and which is swallowed and then reappears in the form of hemorrhaging accompanying vomiting).

In the case of *Plasmodium falciparum* causing complicated malaria or cerebral malaria and also the other severe manifestations, it is a medical emergency when 1% of the red corpuscles (red blood cells) or more are parasitized in an individual who has not yet been immunized against this disease.

In the case of severe malaria, the priority of the treatment is to massively and rapidly (within 24 to 48 hours following commencement of treatment) reduce the parasitemia in order to rule out the lethal prognosis. Once the parasitemia is under control and the vital prognosis is confirmed, a more conventional antimalarial treatment, such as chloroquine or basic quinine hydrochloride, for example, can be administered.

The treatment for severe malaria is difficult to administer orally or rectally, since the patients are often suffering from vomiting accompanied by considerable diarrhea.

Artemisinin, which was isolated in 1972 from the plant *Artemisia annua* (qinghaosu), and has been used for centuries in China, has a powerful antimalarial activity. Derivatives with improved pharmacological properties, such as artemether, arteether and artesunate, are also commercially available.

Artemisinin and derivatives thereof, in particular artesunate, are today part of the active ingredients that are most effective against *Plasmodium falciparum*. However, it is difficult for these compounds to produce complete recovery, and many upsurges are noted. The use of artemisin or derivatives thereof in monotherapy could therefore be a causal factor in the selection of resistant parasitic strains.

The scientific community now recommends the use of combinations of active ingredients, and in particular of combinations of artemisin or derivatives thereof with other antimalarial active ingredients. These polytherapies, known as ACTs (artemisinin-based combination therapies), have been recommended since 2002 by the World Health Organization (WHO). They offer multiple advantages: improved therapeutic efficacy on resistant strains, mutual protection of the two active ingredients against the appearance of resistance, reduction in disease transmission and in resistance propagation.

Several combinations of this type are known.

The combination between artemether and lumefantrine, sold under the name Coartem®, has, for example, been proposed, as has the combination of artesunate and amodiaquine (Arsucam®).

The combination of ferroquine with an artemisinin derivative is described in document WO 2006/111647.

However, the beneficial effect of ACT polytherapies is neither obvious nor foreseeable. For example, the publication by C. Snyder et al., Experimental Parasitology, 115 (2007), 296-300, discloses that the combination of piperaquine with the compound OZ277 appears to be more promising than the combination of piperaquine with an artemisinin derivative such as artemether.

Similarly, the combination of chloroquine and artesunate does not achieve satisfactory efficacy levels (Am. J. Trop. Med. Hyg., 2003, 69(1), 19-25 and Transactions of the Royal Society of Tropical Medicine and Hygiene, 2003, 97, 429-433) and can result in the selection of resistant strains, in particular resistant to chloroquine.

Thus, even though the ACT strategy is recommended by the WHO, the search for new combinations of antimalarial active ingredients is, all the same, not easy and should be continued.

The present invention relates to a combination of a bisthiazolium salt, which is a compound of formula (VI) or a precursor thereof as defined below, and artemisin or a derivative thereof. Among the artemisinin derivatives of use in the present invention, mention may, for example, be made of artesunate, artemether, arteether, hydroartemisinin or dihydroartemisinin.

Such a combination shows an advantageous and unforeseeable synergy and, consequently, is of use in the prevention and/or treatment of malaria, in particular of severe malaria.

BRIEF DESCRIPTION OF THE DRAWINGS

FIG. 1. Change in parasitemia during and after 4 days of ip treatment with artesunate (AS).

FIG. 2. Change in parasitemia during and after 4 days of ip treatment with T3.

FIG. 3. Change in parasitemia during and after 4 days of ip treatment with 0.2 mg/kg/d of T3 and 2.5 mg/kg/d of artesunate (AS).

FIG. 4. Change in parasitemia during and after 4 days of ip treatment with 0.5 mg/kg/d of T3 and 2.5 mg/kg/d of artesunate (AS).

FIG. 5. Change in parasitemia during and after 4 days of ip treatment with 1 mg/kg/d of T3 and 2.5 mg/kg/d of artesunate (AS).

The compounds of formula (VI), and also precursors thereof for the purpose of the present invention, are described in the patent published under number EP 1 196 371. The precursors of the bisthiazolium salts of formula (VI) for the purpose of the present invention correspond to formulae (I), (II), (III), (IV) and (V) of EP 1 196 371. This patent in fact describes precursors of drugs with an antimalarial effect, characterized in that they are products capable of generating bisquaternary ammonium salts and that they correspond to general formula (I):

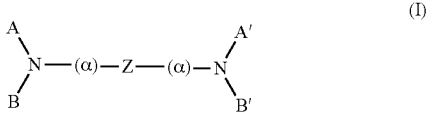

(I)

in which
A and A' are identical to or different from one another and represent:
either, respectively, a group $A_1$ and $A'_1$ of formula:

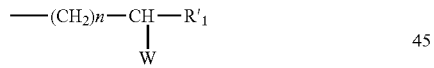

where n is an integer from 2 to 4; $R'_1$ represents a hydrogen atom, a $C_1$ to $C_5$ alkyl radical, optionally substituted with an aryl radical (in particular a phenyl radical), a hydroxyl, an alkoxy, in which the alkyl radical contains from 1 to 5 carbon atoms, or aryloxy (in particular phenoxy);
and W represents a halogen atom chosen from chlorine, bromine or iodine, or a nucleofugal group, such as the tosyl radical $CH_3$—$C_6H_4$—$SO_3$, the mesityl radical $CH_3$—$SO_3$, the $CF_3$—$SO_3$ radical or the $NO_2$—$C_6H_4$—$SO_3$ radical,
or a group $A_2$ which represents a formyl radical —CHO or an acetyl radical —CO—$CH_3$,
B and B' are identical to or different from one another and represent:
either, respectively, the groups $B_1$ and $B'_1$, if A and A' represent, respectively, $A_1$ and $A'_1$, $B_1$ and $B'_1$ representing a group $R_1$ which has the same definition as $R'_1$ above, but cannot be a hydrogen atom,
or, respectively, the groups $B_2$ and $B'_2$, if A and A' represent $A_2$, $B_2$ or $B'_2$ being the group $R_1$ as defined above, or a group of formula:

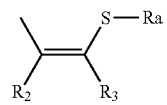

in which —Ra represents an RS— or RCO— group, where R is a linear, branched or cyclic, $C_1$ to $C_6$, in particular $C_1$ to $C_5$, alkyl radical, as appropriate substituted with one or more hydroxyl, alkoxy or aryloxy groups, or an amino group and/or a —COOH or COOM group, where M is a $C_1$ to $C_3$ alkyl; a phenyl or benzyl radical, in which the phenyl radical is, as appropriate, substituted with at least one $C_1$ to $C_5$ alkyl or alkoxy radical, said radicals being optionally substituted with an amino group, or with a nitrogenous or oxygenated heterocycle, a —COOH group or a —COOM group; or a group —$CH_2$-heterocycle, in which the heterocycle has 5 or 6 elements and is nitrogenous and/or oxygenated;
$R_2$ represents a hydrogen atom, a $C_1$ to $C_5$ alkyl radical or a —$CH_2$—COO($C_1$ to $C_5$)alkyl group;
and $R_3$ represents a hydrogen atom; a $C_1$ to $C_5$ alkyl or alkenyl radical, as appropriate substituted with —OH, a phosphate group, an alkoxy radical, in which the alkyl radical is $C_1$ to $C_3$, or aryloxy; or an alkyl (or aryl)carbonyloxy group;
or else $R_2$ and $R_3$ together form a ring containing 5 or 6 carbon atoms; R and $R_3$ may be linked so as to form a ring containing 5- to 7 atoms (carbon, oxygen, sulfur);
α represents:
either a single bond, when A and A' represent A1 and A'1: or when A and A' represent $A_2$, i.e. a —CHO or —$COCH_3$ group, and $B_2$ and $B'_2$ represent:

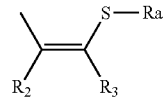

or, when A and A' represent $A_2$ and $B_2$ and $B'_2$ represent $R_1$, a group of formula:

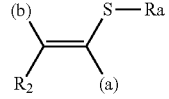

or a group of formula:

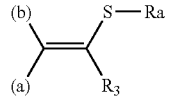

in which (a) represents a bond towards Z and (b) a bond towards the nitrogen atom,
Z represents a $C_6$ to $C_{21}$, in particular $C_{12}$ or $C_{13}$ to $C_{21}$, alkyl radical, as appropriate with insertion of one or more multiple bonds, and/or one or more heteroatoms O and/or S, and/or one or more aromatic rings, and the pharmaceutically acceptable salts of these compounds, with the proviso that $R'_1$ does not represent H or a $C_1$ or $C_2$ alkyl radical, when n=3 or 4, $R_1$ represents a $C_1$ to $C_4$ alkyl radical and Z represents a $C_6$ to $C_{10}$ alkyl radical.

EP 1 196 371 also describes a subgroup of precursor compounds as described above, corresponding to general formula (II):

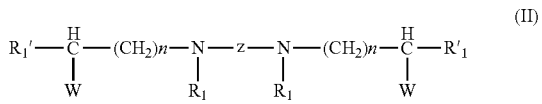

in which $R_1$, $R'_1$, W, n and Z are as defined above.

EP 1 196 371 also describes another subgroup of precursor compounds, constituted of the precursors as described above, for which Z represents a $C_{13}$ to $C_{21}$ alkyl radical.

EP 1 196 371 also describes a subgroup of precursor compounds constituted of the precursors as described in the previous subgroup, for which Z represents a —$(CH_2)_{16}$- group.

EP 1 196 371 describes, in particular, the precursors chosen from N,N'-dimethyl-N,N'-(5-chloropentyl)-1,16-hexadecanediamine dihydrochloride or N,N'-dimethyl-N,N'-(4-chloropentyl)-1,16-hexadecanediamine dihydrochloride.

EP 1 196 371 describes, in addition, a group of precursors, corresponding to general formula (III):

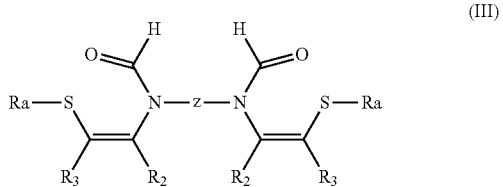

of to general formula (IV):

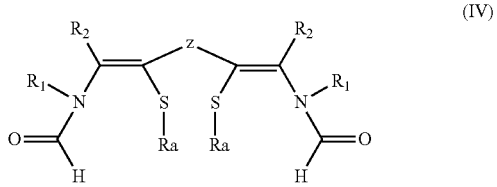

or to general formula (V):

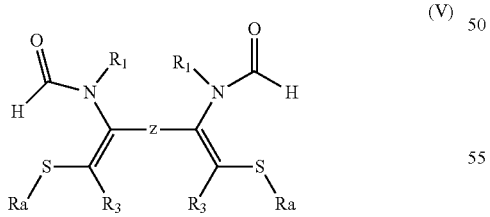

in which Ra, $R_1$, $R_2$, $R_3$ and Z are as defined above.

EP 1 196 371 describes, in particular, precursor compounds of formulae (III), (IV) and (V) as described above, chosen from:
N,N'-diformyl-N,N'-di[1-methyl-2-S-thiobenzoyl-4-methoxybut-1-enyl]-1,12-diaminododecane (TE4c),
N,N'-diformyl-N,N'-di[1-methyl-2-S-(p-diethylaminomethylphenylcarboxy)thio-4-methoxybut-1-enyl]-1,12-diaminododecane (TE4f),
N,N'-diformyl-N,N'-di[1-methyl-2-S-(p-morpholinomethylphenylcarboxy)-thio-4-methoxybut-1-enyl]-1,12-diaminododecane (TE4g),
N,N'-diformyl-N,N'-di[1-methyl-2-S-thiobenzoyl-4-methoxybut-1-enyl]-1,16-diaminohexadecane (TE8),
N,N'-diformyl-N,N'-di[1(2-oxo-4,5-dihydro-1,3-oxathian-4-ylidene)ethyl]1,12-diaminododecane (TE3);
or else from:
N,N'-diformyl-N,N'-di[1-methyl-2-tetrahydrofurfurylmethyldithio-4-hydroxybut-1-enyl]-1,12-diaminododecane (TS3a),
N,N'-diformyl-N,N'-di[1-methyl-2-propyldithio-4-hydroxybut-1-enyl]-1,12-diaminododecane (TS3b),
N,N'-diformyl-N,N'-di[1-methyl-2-benzyldithio-4-hydroxybut-1-enyl]-1,12-diaminododecane (TS3c),
N,N'-diformyl-N,N'-di[1-methyl-2-(2-hydroxyethyl)dithio-4-hydroxybut-1-enyl]-1,12-diaminododecane (TS3d),
N,N'-diformyl-N,N'-di[1-methyl-2-propyldithio-4-methoxybut-1-enyl]-1,12-diaminododecane (TS3d), and
N,N'-diformyl-N,N'-di[1-methyl-2-propyldithioethenyl]-1,12-diaminododecane (TS6b),
or else:
2,17-(N,N'-diformyl-N,N'-dimethyl)diamino-3,16-S-thio-p-methoxybenzoyl-6,13-dioxaoctadeca-2,16-diene (TE9),
2,17-(N,N'-diformyl-N,N'-dibenzyl)diamino-3,16-S-thio-p-methoxybenzoyl-6,13-dioxaoctadeca-2,16-diene (TE10),
ethyl 3,18-(N,N'-diformyl-N,N'-dimethyldiamino-4,17-S-thiobenzoyleicosa-3,17-dienedioate (TE12),
ethyl 3,18-(N,N'-diformyl-N,N'-dibenzyl)diamino-4,17-S-thiobenzoyleicosa-3,17-dienedioate (TE13),
or finally:
2,15-(N,N'-diformyl-N,N'-dimethyl)diamino-1,16-S-thiobenzoylhexadeca-1,15-diene (TE15),
2,15-(N,N'-diformyl-N,N'-dibenzyl)diamino-1,16-S-thiobenzoylhexadeca-1,15-diene (TE16).

EP 1 196 371 describes, furthermore, cyclized derivatives generated from precursors of thiazolium salts, having good antimalarial activity and corresponding to general formula (VI):

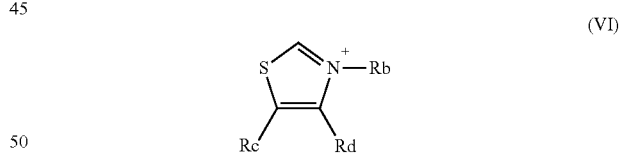

in which
Rb represents $R_1$ or T, T representing the group of formula:

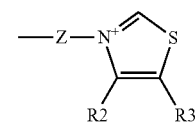

with the proviso that Z does not represent a $C_6$ to $C_8$ alkyl radical, when Rc, Rd, $R_2$ and $R_3$ represent a methyl radical, or when Rc and Rd, on the one hand, and $R_2$ and $R_3$, on the other hand, together form aromatic rings containing 6 carbon atoms, Rd represents R$_2$ or P, P representing the group of formula:

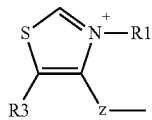

Rc represents R$_3$ or U, U representing the group of formula:

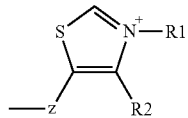

R$_1$, R$_2$, R$_3$ and Z being as defined above,
it being understood that Rb=T, if Rc=R$_3$ and Rd=R$_2$; Rd=P, if Rc=R$_3$ and Rb=R$_1$; and Rc=U, if Rb=R$_1$ and Rd=R$_2$.

According to the present invention, the compounds of formula (VI) may be in the form of a free base, of a salt, of a hydrate or of a solvate.

In particular, EP 1 196 371 mentions, among the cyclized derivatives described above, the derivatives chosen from:
1,12-dodecamethylenebis[4-methyl-5-(2-hydroxyethyl)thiazolium]dibromide (T3);
1,12-dodecamethylenebis[4-methyl-5-(2-methoxyethyl)thiazolium]diiodide (T4);
1,12-dodecamethylenebis(4-methylthiazolium)diiodide (T6);
1,16-hexadecamethylenebis[4-methyl-5-(2-methoxyethyl)thiazolium]diiodide (T8);
3,10-dioxadodecamethylenebis[5-(1,4-dimethyl)thiazolium]diiodide (T9);
3,10-dioxadodecamethylenebis[5-(1-benzyl-4-methyl)thiazolium]dibromide (T10);
dodecamethylenebis[5-(1-methyl-4-ethoxycarbonylethyl)thiazolium]diiodide (T12);
dodecamethylenebis[5-(1-methyl-4-ethoxycarbonylethyl)thiazolium]dibromide (T13);
dodecamethylenebis[4-(1-methyl)thiazolium]diiodide (T15);
dodecamethylenebis[4-(1-benzyl)thiazolium]dibromide (T16).

Finally, EP 1 196 371 describes the process for obtaining the bisthiazolium salts and bisthiazolium precursors mentioned above, in particular the synthesis of the compounds of formula (VI) such as T3, T4, T6, T8, T9, T10, T12, T13, T15 and T16. In particular, the synthesis of T3 is described on page 18 of EP 1 196 371. Similarly, the antimalaria activity of the T3 compound is described in Table 13, page 28 of this same document.

Thus, the invention relates to a combination comprising, as active ingredients, a bisthiazolium salt, which is a compound of formula (VI) or a precursor thereof, as described above, and artemisinin or a derivative thereof.

According to a second subject, the invention relates to a combination of a bisthiazolium salt, which is a compound of formula (VI) or a precursor thereof, as described above, and artesunate.

According to a third subject, the invention relates to a combination of a bisthiazolium salt, which is a compound of formula (VI), chosen from:
1,12-dodecamethylenebis[4-methyl-5-(2-hydroxyethyl)thiazolium]dibromide (T3);
1,12-dodecamethylenebis[4-methyl-5-(2-methoxyethyl)thiazolium]diiodide (T4);
1,12-dodecamethylenebis(4-methylthiazolium)diiodide (T6);
1,16-hexadecamethylenebis[4-methyl-5-(2-methoxyethyl)thiazolium]diiodide (T8);
3,10-dioxadodecamethylenebis[5-(1,4-dimethyl)thiazolium]diiodide (T9);
3,10-dioxadodecamethylenebis[5-(1-benzyl-4-methyl)thiazolium]dibromide (T10);
dodecamethylenebis[5-(1-methyl-4-ethoxycarbonylethyl)thiazolium]diiodide (T12);
dodecamethylenebis[5-(1-methyl-4-ethoxycarbonylethyl)thiazolium]dibromide (T13);
dodecamethylenebis[4-(1-methyl)thiazolium]diiodide (T15);
dodecamethylenebis[4-(1-benzyl)thiazolium]dibromide (T16);
and artesunate.

According to a fourth subject, the invention relates to a combination of a bisthiazolium salt of formula (VI), which is 1,12-dodecamethylenebis[4-methyl-5-(2-hydroxyethyl)thiazolium dibromide (T3), and artesunate.

In these subjects, each of the active ingredients is used at a concentration that reflects their respective potency in curing the infection. In each of the combinations, the respective amounts of the compounds depend on these active doses.

The 1,12-dodecamethylenebis[4-methyl-5-(2-hydroxyethyl)thiazolium]dibromide (T3) present in the combinations according to the invention has the structure which follows:

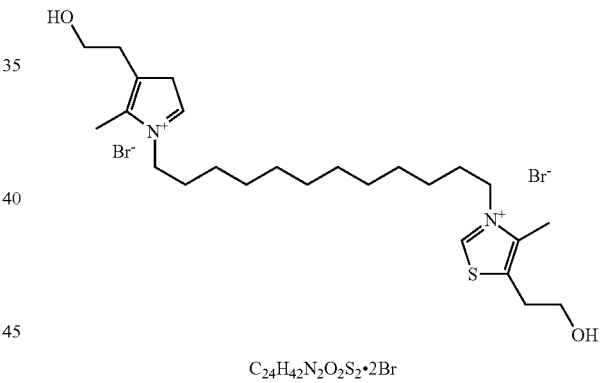

$C_{24}H_{42}N_2O_2S_2 \cdot 2Br$

The artesunate present in the combinations according to the invention has the formula:

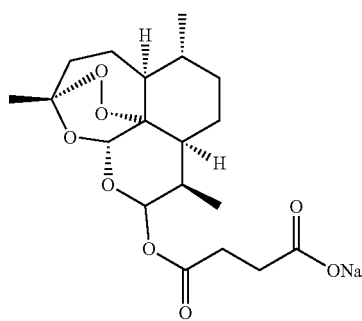

A subject of the invention is also a pharmaceutical composition comprising, as active ingredient, a combination of a bisthiazolium salt of formula (VI) or a precursor thereof, in particular T3, and artemisinin or a derivative thereof, in particular artesunate, as defined above.

Such a pharmaceutical composition contains therapeutically effective doses of a bisthiazolium salt, which is a compound of formula (VI) or a precursor thereof, and of artemisinin or of derivatives thereof, and also at least one pharmaceutically acceptable excipient. Said excipients are chosen, according to the pharmaceutical form and the method of administration desired, from the usual excipients which are known to those skilled in the art. The ranges of proportions of each of the compounds are defined according to the doses thereof which exert an antimalarial activity in monotherapy and reflect their respective potency in curing the infection.

The appropriate unit administration forms comprise oral forms such as tablets, soft or hard gel capsules, powders, granules and oral solutions or suspensions, sublingual, buccal, intratracheal, intraocular or intranasal administration forms, forms for administration by inhalation, topical, transdermal, subcutaneous, intramuscular or intravenous (bolus or perfusion) administration forms, rectal administration forms, and implants. For topical application, the compounds according to the invention may be used in creams, gels, ointments or lotions.

Administration routes envisaged are oral, rectal and parenteral routes, in particular the muscular, intrarectal and intravenous route, and especially via a drip.

For parenteral administration, use is made of aqueous suspensions, isotonic saline solutions or sterile and injectable solutions which contain pharmacologically compatible dispersing agents and/or wetting agents, for example propylene glycol or butylene glycol. The suspensions may also contain, if necessary, antioxidant adjuvants, or the active ingredients according to the invention may be diluted in appropriate solutions, such as glucose or NaCl, in order to be subsequently administered via a drip.

With parenteral administration, and in particular via a drip, the preferred daily doses of each of the two active ingredients of the combination according to the invention are as indicated above:

bisthiazolium salt of formula (VI), in particular T3: between 0.01 and 3 mg/kg;
artemisinin or a derivative thereof, in particular artesunate: between 1 and 5 mg/kg.

There may be specific cases where higher or lower doses are suitable; such dosages do not depart from the context of the invention. According to the usual practice, the dosage suitable for each patient is determined by the physician according to the method of administration and the weight and response of said patient.

The combination according to the invention is intended to be administered for 1 to 4 consecutive days, as one or more daily intakes of each of the two active ingredients, preferably 1 to 3 intakes (oral or rectal) or bolus(es) per day. This treatment time preferably limited to 4 days or less is particularly advantageous for massively and rapidly reducing the parasitemia and allowing the patient, having warded off his or her lethal prognosis, to be subsequently treated against the malaria per se. This subsequent treatment can be carried out by monotherapy with artemisinin derivatives, by any other known treatment for malaria, but also by administration of the combination according to the invention.

An example of dosage and of method of administration may be 2.4 mg/kg/day of artesunate and 1 mg/kg/day of T3 for the first 24 hours of treatment of the patient (D1) exhibiting severe malaria, and then 1.2 mg/kg/day of artesunate and 0.8 mg/kg/day of T3 for the next 48 hours (D2 and D3), the artesunate and the T3 being administered via a drip, in a single drip bag at D1 and in separate drip bags at D2 and D3.

The administration of each of the two active ingredients may be carried out simultaneously, or else separately or spread out over time (sequential administration).

When the administration is carried out simultaneously, the two active ingredients may be combined within a single pharmaceutical form (fixed combination), such as a tablet or a gel capsule suitable for oral administration, or in the same drip bag, or a formulation suitable for intrarectal administration.

The two active ingredients of the combination according to the invention may also, whether the administration thereof is simultaneous or nonsimultaneous, be present in distinct pharmaceutical forms. To this effect, the combinations according to the invention may be in the form of a kit comprising, on the one hand, the compound of formula (VI) or a precursor thereof, in particular T3 or a salt, hydrate or solvent, and, on the other hand, artemisinin or a derivative thereof, in particular artesunate, said compound of formula (VI) such as T3 and the artesunate being in distinct compartments and being intended to be administered simultaneously, separately or in a manner spread out over time (sequential administration).

By way of example, a unit administration form of T3 in tablet form may comprise the following components:

| | |
|---|---|
| T3 | 6 mg |
| Mannitol | 224 mg |
| Sodium croscaramellose | 6 mg |
| Maize starch | 15 mg |
| Hydroxypropylmethylcellulose | 2 mg |
| Magnesium stearate | 3 mg |

Equally, by way of example, a unit administration form of artesunate in tablet form may comprise 50 or 100 mg of artesunate and customary excipients, for example lactose, croscarmellose, anhydrous colloidal silica, microcrystalline cellulose and magnesium stearate.

Equally, by way of example, a unit administration form comprising a combination of artesunate and T3 may comprise 1.5 mg of T3 and 50 mg of artesunate, and also customary excipients such as those mentioned above, the daily dose for an adult being achieved in 4 intakes of one tablet or in one intake of 4 tablets.

The same dosages of T3, of artesunate, or of T3 and artesunate combination are used for the unit forms for rectal administration, with the excipients known to those skilled in the art.

For a method of administration by parenteral injection, a unit administration form of T3 may comprise 1 mg of T3 in a vial, for example, and also customary excipients well known to those skilled in the art, such as glycerol and a phosphate buffer, the vial being designed for 10 kg of body weight.

Equally, by way of example, a unit administration form of artesunate and of T3 in a vial may comprise 24 mg of artesunate and 1 mg of T3, and also customary excipients such as those mentioned above, the vial being administered at a rate of one vial per 10 kg of body weight.

A subject of the present invention is also a method of treating and/or preventing severe malaria, which comprises the administration, to a patient, of an effective therapeutic dose of at least one thiazolium salt, which is a compound of formula (VI) or a precursor thereof, in particular T3, and of an effective therapeutic dose of artemisinin or a derivative thereof, in particular artesunate, said doses being administered simultaneously or else sequentially to said patient, as is previously described.

The present invention also relates to a method as defined above, for treating and/or preventing malaria, in particular severe malaria.

A subject of the invention is also the use of a combination comprising, as active ingredients, a bisthiazolium salt, which is a compound of formula (VI) or a precursor thereof, as described above, and artemisinin or a derivative thereof, in particular artesunate, for the preparation of a medicament for use in the treatment or prevention of malaria, in particular of severe malaria.

Finally, a subject of the invention is
a kit for the treatment or prevention of severe malaria, comprising, on the one hand, at least one bisthiazolium salt, which is a compound of formula (VI) or a precursor thereof, and, on the other hand, at least artemisinin or a derivative thereof, in particular artesunate, said compound of formula (VI)/precursor and artemisinin/derivative being in distinct drip bags or compartments and being intended to be administered simultaneously or sequentially, and a kit as defined above, characterized in that it comprises, on the one hand, at least 1,12-dodecamethylenebis[4-methyl-5-(2-hydroxyethyl)thiazolium]dibromide, and, on the other hand, at least artesunate.

The combination according to the invention was the subject of pharmacological and biochemical tests in vivo in mice infected with a *plasmodium* of *Plasmodium falciparum* type (strain *Plasmodium vinckei petteri*), making it possible to demonstrate its efficacy and the synergistic effect that it provides, for the treatment of malaria.

In Vivo Measurement of the Antimalarial Activity, in Mice Infected with *Plasmodium vinckei petteri*, of the Combination of 1,12-dodecamethylenebis[4-methyl-5-(2-hydroxyethyl)thiazolium]dibromide (T3) with Artesunate Definitions of the Terms Used in this Test:
$ED_{50}$=dose in mg/kg/day which brings about a 50% decrease in parasitaemia, observed in the infected mice,
$ED_{90}$=dose in mg/kg/day which brings about a 90% decrease in parasitaemia, observed in the infected mice,
ip=intraperitoneal administration,
iv=intravenous administration,
ir=intrarectal administration.

1. Description of the In Vivo Test Used
—Infection of Mice
On day 0 (D0), female "Swiss" mice (OF1, 22-26 g) (Charles River Laboratories France, 59 rue de la Paix, 76410 Saint-Aubin-les-Elbeuf) are inoculated, by iv injection in the caudal vein, with $10^8$ parasitized erythrocytes suspended in 200 µl of NaCl (0.9%). The parasites used are of *Plasmodium vinckei petteri* type (strain 279 BY, supplied by Dr. I Landau, Paris, France).

The mice are acclimatized beforehand for two weeks. They are given food and drink ad libitum.

The injection of $10^8$ parasitized erythrocytes results, at day 1 (D1), in a parasitemia level of between 5% and 10% (7.2%±0.2%). The *Plasmodium vinckei petteri* strain is maintained by weekly infection in mice with $10^7$ to $10^8$ parasitized erythrocytes suspended in a saline phosphate buffer (0.9%) (infection by intraperitoneal administration).

—Preparation of the Solutions of T3 and of Artesunate
The products are dissolved in a 0.3M phosphate buffer (pH=8.1). The final concentration of the T3 solution is between 40 and 200 mg/l depending on the dose. The final concentration of the artesunate solution is between 100 and 500 mg/l depending on the dose.

The products are administered ip. The administration volume is of the order of 100 µl, but depends on the weight of the mouse.

—Treatments
The mice are treated once a day for 4 days, on days D1, D2, D3 and D4 (Peters, W., J. H. Portus, and B. L. Robinson. 1975. The chemotherapy of rodent malaria. XXII. The value of drug-resistant strains of *P. berghei* in screening for blood schizonticidal activity. Ann. Trop. Med. Parasitol. 69:155-171; and: Ancelin M L, Calas M., Bonhoure A., Herbute S, and Vial H., In vivo antimalarial activity of mono and bis quaternary ammonium salts interfering with *Plasmodium* phospholipid metabolism. Antimicrob. Agents Chemother., 2003, 47, 2598-2605). Four mice are used per dose.

The animal is given, by ip administration, according to the case, T3, artesunate or the mixture of the two active ingredients solubilized.

Measurement of the Parasitemia
At the 5th day, a few drops of blood are taken from the tail of the mouse in order to determine the parasitemia by FACS (fluorescence-activated cell sorter) and to perform a blood smear. The parasitemia is first determined by FACS on 20 000 cells. The red blood cells taken for the FACS are fixed with glutaraldehyde and then labeled with a fluorochrome (YOYO1®) which labels DNA and therefore only the parasitized cells (Barkan, D., Ginsburg, H., and Golenser, J. 2000. Optimisation of flow cytometric measurement of parasitaemia in *plasmodium*-infected mice. Int. J. Parasitol. 30: 649-653). The parasitemias below 15% are subsequently recounted on smears. The smears are fixed with methanol and then stained with Giemsa stain. The number of parasitized blood cells is counted under a microscope. The parasitemia is expressed as percentage of infected erythrocytes present in the specimen, on a sample of 2000 cells. The $ED_{50}$ and $ED_{90}$ values are determined at D5. The parasitemia is determined from the 1st to the 10th day of treatment, and then at the 15th, 22nd and 47th days.

The mice for which the smear at D5 reveals no trace of parasites will be checked again for at least one month after the end of the treatment, in order to detect any possible upsurge of parasites. The curative dose is the dose of product which ensures the survival of the entire treated batch of animals after one month.

Determination of $ED_{50}$ Values
0% inhibition corresponds to the mean of the parasitemias observed in the nontreated, infected mice. 100% inhibition corresponds to a very weak or null parasitemia, below 0.01%. The $ED_{50}$ values are determined by linear interpolation of the dose-response curve represented in logarithm of concentrations.

2. Measurement of the Antimalarial Activity of T3 and of Artesunate on a *Plasmodium vinckei petteri* Parasite Strain In Vivo In order to demonstrate a synergistic effect between the two compounds, it is important to know their activity when they are administered alone, in order to combine them at doses close to their $ED_{50}$. The case of parenteral administration thereof corresponds to the clinical situation of severe malaria. In this case, it is important to rapidly reduce the parasitemia over the first days of treatment. At the doses tested, artesunate administered alone does not reduce the parasitemia on the first day, and likewise on the following days (FIG. 1). T3 effectively reduces the parasitemia after 4 days of treatment at a dose of 1 mg/kg/d, but does not prevent an increase in parasitemia after the first day of treatment (FIG. 2).

The $ED_{50}$ values obtained are given in Table 1 which follows:

TABLE I

| | $ED_{50}$ (mg/kg/day) |
|---|---|
| T3 | 0.55 |
| artesunate | >2.5 |

The lower the $ED_{50}$, the better the activity. Thus, T3 alone shows a better activity on the parasitemia (0.55 mg/kg/day) than artesunate alone (>2.5 mg/kg/day). Furthermore, T3 alone, at a dose of 0.5 mg/kg/day, allows complete recovery after one month (results not shown), whereas artesunate alone, at a dose of 2.5 mg/kg/day, does not.

3. Measurement of the Antimalarial Activity of the T3/Artesunate Combination on a *Plasmodium vinckei petteri* Parasite Strain In Vivo For this combination study, the dose of 2.5 mg/kg/d of artesunate (slightly below but close to the $ED_{50}$) was chosen, the dose of 0.5 mg/kg/d being completely inactive on the parasitemia at 4 days. T3 was evaluated in combination at a lower dose, close to and above the $ED_{50}$, i.e. 0.2, 0.5 and 1 mg/kg/d.

Surprisingly, as indicated in FIGS. 3, 4 and 5, the combination comprising T3 (at all the abovementioned doses) with artesunate present at a dose of 2.5 mg/kg/day makes it possible to significantly reduce the level of parasitemia, by comparison with the separate administration of T3 alone or of artesunate alone. In particular, it is important to note that, 24 h after the first administration (day 2) and whatever the dose of T3 administered, a decrease in the parasitemia of the mice is observed, whereas, at this time point, the products administered individually are inactive. Table II (and FIGS. 3, 4 and 5) give the average of the parasitemias recorded at this day 2 (4 animals per dose). It should be noted that there is a statistically synergistic effect 24 hours after the first administration (day 2) for T3 at doses of 0.2, 0.5 and 1 mg/kg in combination with artesunate at a dose of 2.5 mg/kg. This very significant synergistic effect after the first day of treatment is particularly important in the case of the treatment of severe malaria, where the clinician is precisely seeking a massive and rapid reduction in the patient's parasitemia in order to ward off the lethal prognosis.

TABLE II

| Artesunate (mg/kg/d) | T3 (mg/kg/d) | parasitaemia D1 | parasitaemia D2 | parasitaemia D5 |
|---|---|---|---|---|
| 0 | 0 | 7.20% | 26.90% | death |
| 2.5 | 0 | 7.00% | 32.90% | 53.20% |
| 2.5 | 0.2 | 8.10% | 5.70% | 54.90% |
| 2.5 | 0.5 | 8.30% | 3.40% | 15.10% |
| 2.5 | 1 | 6.10% | 5.10% | 10.70% |
| 0 | 0.2 | 6.60% | 35.00% | 55.20% |
| 0 | 0.5 | 7.80% | 34.00% | 56.80% |
| 0 | 1 | 7.20% | 27.90% | 19.40% |

Starting from the T3 dose of 0.5 mg/kg/day combined with 2.5 mg/kg/day artesunate, the parasitemia is maintained at its initial value before treatment, throughout the duration of the treatment, whereas the individual administrations of products do not enable this (Table II, FIGS. 3, 4 and 5).

The T3 compound is responsible for the predominant effect on complete recovery of the mice after one month. The coadministration of artesunate at 2.5 mg/kg/day does not improve the curative dose obtained with T3 alone.

Table III summarizes the results discussed above.

TABLE III

| | | T3 (mg/kg/d) | | |
|---|---|---|---|---|
| Artesunate (mg/kg/d) | 0 | 0.2 | 0.5 | 1 |
| 0 | 0 | Dose-dependent reduction in parasite growth from D3 to D5 | Dose-dependent reduction in parasite growth from D3 to D5, curative dose | |
| | 2.5 | Dose-dependent reduction in parasite growth from D3 to D5 | Reduction in parasitemia compared to D0, at D1 | Reduction in parasitemia compared to D0, throughout the duration of the treatment |

Thus, when the 2 active ingredients are administered in combination, the parasitemia decreases significantly during the first 4 days of treatment. The effect is very much greater at doses comparable to, or even lower than, those determined for the administration of each of the two active ingredients taken individually.

In particular when T3 is administered in combination with artesunate, the artesunate being present at a dose of at least 2.5 mg/kg/day, a beneficial effect is observed on the decrease in parasitemia. It is therefore understood that the combination of the two active ingredients is particularly effective in a window defined by the minimum dose of one of the compounds and the ratio of one of the compounds relative to the other, within this window.

The results obtained in vivo in mice infected with *P. vinckei petteri* prove that the combination according to the invention, of artemisinin or a derivative thereof (in particular, artesunate), and of a bisthiazolium salt, which is a compound of formula (VI), in particular T3, is advantageous for the treatment of malaria, and in particular of severe malaria.

The invention claimed is:

1. A combination comprising, as active ingredients, a bisthiazolium salt, which is a compound of formula (VI):

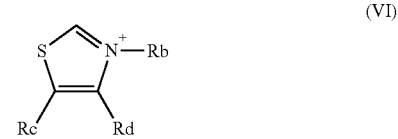

(VI)

in which

Rb represents:
a group $R_1$ which itself represents a $C_1$ to $C_5$ alkyl radical, optionally substituted with an aryl radical, a hydroxyl, an alkoxy, in which the alkyl radical contains from 1 to 5 carbon atoms, or aryloxy, or else a group T, T representing the group of formula:

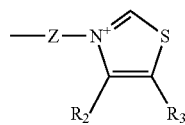

in which:
$R_2$ represents a hydrogen atom, a $C_1$ to $C_5$ alkyl group or a —$CH_2$—COO—($C_1$ to $C_5$)alkyl group;
$R_3$ represents a hydrogen atom, a $C_1$ to $C_5$ alkyl or alkenyl radical, optionally substituted with —OH, a phosphate group, an alkoxy radical, in which the alkyl radical is $C_1$ to $C_3$, or aryloxy; or an alkyl (or aryl)carbonyloxy group;
or else $R_2$ and $R_3$ together form a ring containing 5 or 6 carbon atoms; $R_2$ and $R_3$ may be linked so as to form a ring or a heterocycle containing 5 to 7 members, optionally comprising one or more heteroatoms O and/or S;
Z represents a $C_6$ to $C_{21}$ alkylene radical, optionally with insertion of one or more multiple bonds, and/or one or more heteroatoms O and/or S, and/or of one or more aromatic rings, and the pharmaceutically acceptable salts of these compounds,
with the proviso that Z does not represent a $C_6$ to $C_8$ alkylene radical, when Rc, Rd, $R_2$ and $R_3$ represent a methyl radical, or when Rc and Rd, on the one hand, and $R_2$ and $R_3$, on the other hand, together form aromatic rings containing 6 carbon atoms;
Rd represents $R_2$ as defined above or P, P representing the group of formula:

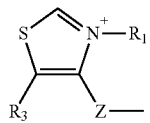

Rc represents $R_3$ as defined above or U, U representing the group of formula:

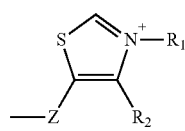

wherein Rb=T, if Rc=$R_3$ and Rd=$R_2$; Rd=P, if Rc=$R_3$ and Rb=$R_1$; and Rc=U, if Rb=$R_1$, and Rd=$R_2$, in the form of a free base or of a salt,
or a precursor thereof chosen from the compounds of formulae (I) to (V),
the compound (I) corresponding to the formula:

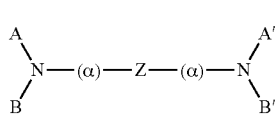

in which
A and A' are identical to or different from one another and represent:
either, respectively, a group $A_1$ and $A'_1$ of formula:

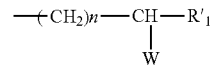

where n is an integer from 2 to 4; $R'_1$ has the same definition as $R_1$ above, but can also be a hydrogen atom;
and W represents a halogen atom chosen from chlorine, bromine or iodine, or a nucleofugal group selected from the group consisting of $CH_3$—$C_6H_4$—$SO_3$, $CH_3$—$SO_3$, $CF_3$—$SO_3$ and $NO_2$—$C_6H_4$—$SO_3$,
or a group $A_2$ which represents a formyl radical —CHO or an acetyl radical —CO—$CH_3$,
B and B' are identical to or different from one another and represent:
either, respectively, the groups $B_1$ and $B'_1$, if A and A' represent, respectively, $A_1$ and $A'_1$, $B_1$ and $B'_1$ representing a group $R_1$, as defined above,
or, respectively, the groups $B_2$ and $B'_2$, if A and A' represent $A_2$, $B_2$ or $B'_2$ being the group $R_1$ as defined above, or a group of formula:

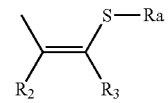

in which —Ra represents an RS— or RCO— group, where R is a linear, branched or cyclic, $C_1$ to $C_6$ alkyl radical, optionally substituted with one or more hydroxyl, alkoxy or aryloxy groups, or an amino group and/or a —COOH or COOM group, where M is a $C_1$ to $C_3$ alkyl; a phenyl or benzyl radical, in which the phenyl radical is optionally substituted with at least one $C_1$ to $C_5$ alkyl or alkoxy radical, said radicals being optionally substituted with an amino group, or with a nitrogenous or oxygenated heterocycle, a —COOH group or a —COOM group; or a group —$CH_2$-heterocycle, in which the heterocycle has 5 or 6 elements and is nitrogenous and/or oxygenated;
$R_2$ represents a hydrogen atom, a $C_1$ to $C_5$ alkyl radical or a —$CH_2$—COO($C_1$ to $C_5$)alkyl group;
and $R_3$ represents a hydrogen atom; a $C_1$ to $C_5$ alkyl or alkenyl radical, as appropriate substituted with —OH, a phosphate group, an alkoxy radical, in which the alkyl radical is $C_1$ to $C_3$, or aryloxy; or an alkyl (or aryl) carbonyloxy group;
or else $R_2$ and $R_3$ together form a ring containing 5 or 6 carbon atoms; R and $R_3$ may be linked so as to form a ring containing 5- to 7 atoms (carbon, oxygen, sulphur);
α represents:
either a single bond, when A and A' represent $A_1$ and $A'_1$: or when A and A' represent $A_2$, which is a —CHO or —$COCH_3$ group, and $B_2$ and $B'_2$ represent:

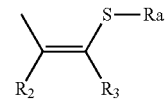

or, when A and A' represent $A_2$ and $B_2$ and $B'_2$ represent $R_1$, a group of formula:

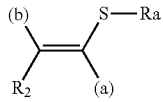

or a group of formula:

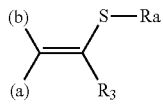

in which (a) represents a bond towards Z and (b) a bond towards the nitrogen atom, Z represents a $C_6$ to $C_{21}$ alkylene radical, optionally with insertion of one or more multiple bonds, and/or one or more heteroatoms O and/or S, and/or one or more aromatic rings, and the pharmaceutically acceptable salts of these compounds, with the proviso that $R'_1$ does not represent H or a $C_1$ or $C_2$ alkyl radical, when n=3 or 4, $R_1$ represents a $C_1$ to $C_4$ alkyl radical and Z represents a $C_6$ to $C_{10}$ alkylene radical;

the compound (II) corresponding to the formula:

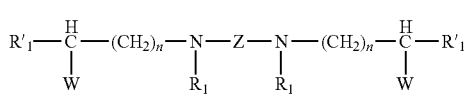

the compound (III) corresponding to the formula:

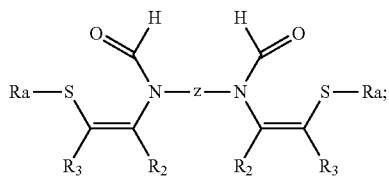

the compound (IV) corresponding to the formula:

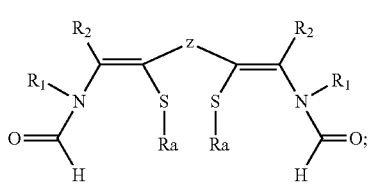

the compound (V) corresponding to the formula:

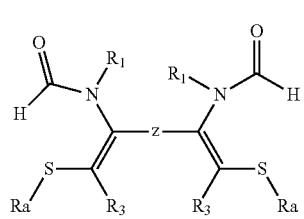

in which Ra, $R_1$, $R'_1$, $R_2$, $R_3$, W, n and Z are as defined above,
and
artemisinin or a derivative thereof, chosen from artesunate, artemether, arteether, hydroartemisinin or dihydroartemisinin,
for the treatment and/or prevention of severe malaria.

2. The combination of claim 1, wherein the bisthiazolium salt of formula (VI), is chosen from the group consisting of:
1,12-dodecamethylenebis[4-methyl-5-(2-hydroxyethyl) thiazolium] dibromide;
1,12-dodecamethylenebis[4-methyl-5-(2-methoxyethyl) thiazolium] diiodide;
1,12-dodecamethylenebis(4-methylthiazolium) diiodide;
1,16-hexadecamethylenebis[4-methyl-5-(2-methoxyethyl)thiazolium] diiodide;
3,10-dioxadodecamethylenebis[5-(1,4-dimethyl)thiazolium] diiodide;
3,10-dioxadodecamethylenebis[5-(1-benzyl-4-methyl) thiazolium] dibromide;
dodecamethylenebis[5-(1-methyl-4-ethoxycarbonylethyl) thiazolium] diiodide;
dodecamethylenebis[5-(1-methyl-4-ethoxycarbonylethyl) thiazolium] dibromide;
dodecamethylenebis[4-(1-methyl)thiazolium] diiodide; and
dodecamethylenebis[4-(1-benzyl)thiazolium] dibromide.

3. The combination of claim 1, wherein each of the active ingredients is administered simultaneously or sequentially.

4. A pharmaceutical composition comprising therapeutically effective doses of artemisinin or of a derivative thereof, and of at least one bisthiazolium salt of formula (VI), or a precursor thereof, as defined in claim 1, and also at least one pharmaceutically acceptable excipient, for the treatment of severe malaria.

5. The pharmaceutical composition of claim 4, wherein the bisthiazolium salt of formula (VI) is 1,12-dodecamethylenebis[4-methyl-5-(2-hydroxyethyl)thiazolium] dibromide.

6. The pharmaceutical composition according of claim 5 wherein the artemisinin derivative is artesunate.

7. The pharmaceutical composition of claim 6 wherein the composition is suitable for oral, rectal or injectable administration.

8. A method of treating severe malaria comprising administering to a patient in need thereof the combination of claim 1.

9. A kit for the treatment of severe malaria, comprising, on the one hand, at least one bisthiazolium salt, which is a compound of formula (VI) or a precursor thereof, and, on the other hand, at least artemisinin or a derivative thereof, as defined in claim 1, said compound of formula (VI) or a precursor thereof and the artemisinin or a derivative thereof being in distinct compartments and being intended to be administered simultaneously or sequentially.

10. The kit of claim 9 comprising, on the one hand, at least 1,12-dodecamethylenebis[4-methyl-5-(2-hydroxyethyl)thiazolium] dibromide, and, on the other hand, at least artesunate.

11. The combination of claim 1 wherein said aryl radical in the definition of group $R_1$ is a phenyl radical.

12. The combination of claim 1 wherein said aryloxy in the definition of group $R_1$ is a phenyloxy.

13. The combination of claim 1 wherein Z represents a $C_{13}$ to $C_{21}$ alkylene radical.

14. The pharmaceutical composition of claim 6 wherein the composition is suitable for intravenous injection.

15. The pharmaceutical composition of claim 14 wherein the composition is suitable for intravenous injection in the form of a drip.

* * * * *